United States Patent
Montal et al.

(10) Patent No.: US 6,251,854 B1
(45) Date of Patent: Jun. 26, 2001

(54) N-METHYL-D-ASPARTATE RECEPTOR CHANNEL BLOCKERS AND METHOD FOR IDENTIFYING SUCH

(76) Inventors: Mauricio Montal, 1476 Castellana Rd., La Jolla, CA (US) 92037; Antonio Ferrer-Montiel, Department of Biochemistry and Molecular Biology, Miguel-Herandez University, c/ Monovar s/n, E-03206 Elche, Alicante; Jaime Merino, Department of Biochemistry and Molecular Biology, Facultad de Ciencias, Universidad de Extremadura, Av. Elvas s/n, 06080 Badajoz, both of (ES); Sylvie Blondelle, 12435 Carmel Pointe, San Diego, CA (US) 92130; Richard Houghten, 4939 Rancho Viejo, el Mar, CA (US) 92014

(*) Notice: Subject to any disclaimer, the term of this patent is extended or adjusted under 35 U.S.C. 154(b) by 0 days.

(21) Appl. No.: 09/381,434
(22) PCT Filed: Mar. 20, 1998
(86) PCT No.: PCT/US98/05800
 § 371 Date: Dec. 6, 1999
 § 102(e) Date: Dec. 6, 1999
(87) PCT Pub. No.: WO98/41223
 PCT Pub. Date: Sep. 24, 1998

Related U.S. Application Data
(60) Provisional application No. 60/042,703, filed on Mar. 20, 1997.

(51) Int. Cl.$^7$ ............... A61K 38/00; A61K 38/02; A61K 31/535; A01N 37/52
(52) U.S. Cl. ............... 514/2; 514/17; 514/18; 514/212; 514/238; 514/634
(58) Field of Search ............... 514/2, 17, 18, 514/19, 212, 238, 634

(56) References Cited

U.S. PATENT DOCUMENTS

| | | | | |
|---|---|---|---|---|
| 5,011,834 | * | 4/1991 | Weber et al. | 514/212 |
| 5,093,525 | * | 3/1992 | Weber et al. | 564/238 |
| 5,190,976 | * | 3/1993 | Weber et al. | 514/634 |

\* cited by examiner

*Primary Examiner*—Avis M. Davenport
(74) *Attorney, Agent, or Firm*—Foley & Lardner

(57) ABSTRACT

Compounds that provide protection against excitotoxic neuronal damage are selected from the group consisting of Arg-rich oligopeptides and compounds of formula 1:

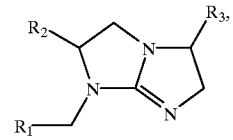

where $R_1$ is alkyl, alkenyl, or hydroxyalkyl, aminoalkyl, or alkoxy-alkyl; and $R_2$ and $R_3$ are each natural or artificial amino acid side chains.

15 Claims, 4 Drawing Sheets

ND-METHYL-D-ASPARTATE RECEPTOR
CHANNEL BLOCKERS AND METHOD FOR
IDENTIFYING SUCH

This application is a 35 U.S.C. 371 application of PCT/US 98/05800 filed Mar. 20, 1998.

STATEMENT OF FEDERAL SUPPORT

Support for this work was provided under Grant Number 17-93-C-3100 by the United States Army Medical Research Command and under Grant Number GM-49711 by the National Institutes of Health. The Government may have certain rights in this invention.

FIELD OF THE INVENTION

The invention relates to compounds which inhibit excessive activation of glutamate receptors, particularly those in the brain. More specifically, the invention relates to compounds which block activity at N-methyl-D-aspartate receptor channels in cerebral neuronal cells.

BACKGROUND OF THE INVENTION

Excitotoxic neuronal death is a phenomenon which is associated with several chronic neurodegenerative conditions (e.g., AIDS-associated dementia, Alzheimer's disease, epilepsy, Parkinson's disease, Huntington's disease, neuropathic pain syndrome, encephalopathy, and other dementias) as well as acute cerebral dysfunctions (e.g., stroke, cerebral ischemia, hypoxia, anoxia, carbon monoxide poisoning and hypoglycemia). Excitotoxic neuronal death is triggered primarily by massive $Ca^{2+}$ influx arising from overactivation of glutamate receptor channels of the N-methyl-D-aspartate ("NMDA") subtype (see e.g., "The NMDA Receptor", Collingridge, G. L., ed. (Oxford Univ. Press, 1996); and Lipton and Rosenberg, *New Engl. J. Med.* (1994) 330:613–22).

Clinical use of existing non-peptidic NMDA specific channel blockers (e.g., phenyclipine (PCP) and dizolcipine (MK-801)) is limited by the frequent occurrence of adverse side effects which impair cognitive functions in treated patients. Clinical use of less specific channel blockers (e.g., dextrorphan and dextromethorphan) is limited by side effects stemming from their interactions with receptors other than NMDA receptors. At present, NMDA-specific peptidic channel blockers are not available.

SUMMARY OF THE INVENTION

A realistic strategy for neuroprotection (i.e., protection of neuronal cells from injury or death resulting from pathologic events such as excessive $Ca^{2+}$ influx) requires intervention at specific targets in neuronal cells. The NMDA receptor channel is of particular interest in this regard due to its role as a primary effector in mediating the influx of calcium that activates intracellular signaling cascades which lead to cell death.

Open channel blockers of the NMDA receptor, which act preferentially on overactivated receptors, have proved to be valuable in preventing neuronal cell death after excitotoxic insults (for example, memantine is prescribed for the treatment of Parkinson's disease). This neuroprotectant effect has been documented in vitro for hippocampal, cortical and retinal ganglion cell neurons, in animal stroke models and in humans (Miller et al., *Pharmacopsychiatry*, (1995) 28:113–24).

The compounds of the invention act as open channel blockers and as neuroprotectants at concentrations that compare favorably with those used clinically for memantine therapy. Advantageously, the compounds of the invention are relatively small, simple molecules which are simple to manufacture and are less immunogenic than known neuroprotectant drugs.

Structurally, the compounds of the invention consist of arginine-rich oligopeptides or compounds of formula 1

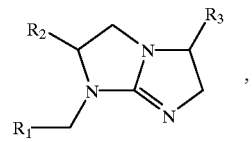

where $R_1$ is alkyl, alkenyl, or hydroxyalkyl, aminoalkyl, or alkoxy-alkyl; and $R_2$ and $R_3$ are each natural or artificial amino acid side chains; and pharmaceutically acceptable salts thereof. Preferred compounds of the invention block the NMDA receptor channel with a $K_i$ of about 10–100 nM or less and are selective for NMDA receptors, having little or no effect on other receptors. Channel blockade by the compounds of the invention is voltage-dependent indicating that the compounds act as open channel blockers.

DETAILED DESCRIPTION OF THE INVENTION

Figure 1:
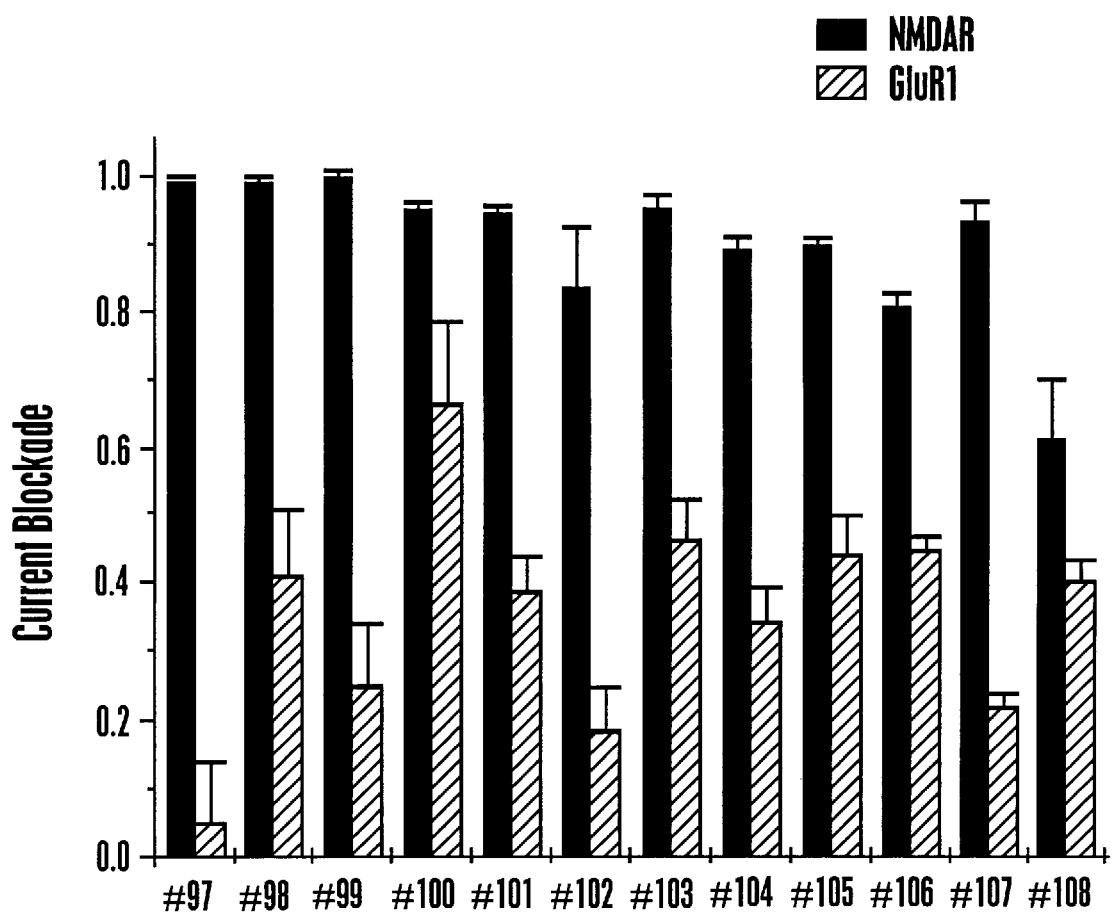
FIG. 1 is a bar graph which depicts the extent of current blockade achieved by various peptides of the invention acting on NMDA receptors ("NMDAR", solid bars) and glutamate receptors of the AMPA-receptor subunit GluR1 type ("GluR1", shaded bars) in amphibian oocytes. Each tested peptide is identified by sequence and test number along the bottom axis of the graph. Current blockade is expressed as a function of the extent of current reduction as compared to current produced in control amphibian oocytes.

Definitions:

The term "NMDA channel blocker" as used herein refers to a compound which binds selectively to the NMDA channel/receptor and is capable of blocking or inhibiting the current through the channel by a detectable amount. The NMDA channel blocker.is preferably specific for the open channel, and preferably blocks at least 50% of the current through the receptor, more preferably at least about 75%, more preferably at least about 95%. The term "natural amino acid" refers to the naturally occurring L-amino acids, Ala, Gly, Ser, Val, Leu, Ile, Met, Pro, Phe, Trp, Thr, Cys, Tyr, Asp, Glu, Asn, Gln, Lys, Arg, and His. The term "artificial amino acid" refers to D-isomers of amino acids, for example D-Arg, D-Phe, and the like; homologs such as homoarginine, 5-aminopentylglycine (homoLys), norvaline, and the like; substituted analogs having 1–3 halo, lower alkyl, trihalomethyl, nitro, hydroxy, amino, acetyl, phenyl, pyridyl, or naphthyl moieties, such as t-butylglycine, iodoPhe, 0-methyl-L-Tyr, naphthylalanine, and the like; and combinations thereof, such as D-naphthylalanine, 3-pyridylalanine, and the like. The term "aromatic amino acid" as used herein refers to a natural or artificial amino acid that comprises an aromatic ring, such as Phe, D-Phe, Tyr, Trp, D-(3-pyridyl)alanine, and the like. The term "guanidinium-containing amino acid" refers to a natural or artificial amino acid that comprises a guanidinium moiety (—NH—C((=NH)—NH$_2$). "Amino acid side chain" refers to the moiety bound to the alpha carbon of an amino acid, for example CH$_3$ in the case of Ala.

The terms "lower alkyl" and "alkyl" as used herein refer to a saturated hydrocarbon moiety having from one to six carbon atoms, which can be straight or branched or cyclic, for example, methyl, ethyl, propyl, isopropyl, butyl, t-butyl, cyclohexyl, cyclopentylmethylene, and the like. The term "alkylene" refers to a divalent alkyl moiety such as ethylene (—CH$_2$CH$_2$—), propylene (—CH$_2$CH$_2$CH$_2$—), and the like. The term "alkenyl" refers to an unsaturated hydrocarbon moiety having at least one C=C double bond, containing from 2 to 6 carbon atoms. The term "hydroxyalkyl" refers to a moiety of the form —R—OH, where R is alkyl. The term "aminoalkyl" as used herein refers to a moiety of the form —R—NH$_2$, where R is alkyl. The term "acyl" as used herein refers to a moiety of the formula —C(O)R, where R is lower alkyl as defined above. The term "aryl" refers to phenyl, naphthyl, and heterocyclic compounds having up to two rings and containing up to three heteroatoms selected from nitrogen, oxygen, and sulfur. The term "aralkyl" refers to a moiety of the form Ar—R—, where Ar is aryl and R is alkylene.

The term "halo" refers to fluoro, chloro, bromo, and iodo.

The term "pharmaceutically acceptable salt" refers to an acid addition salt using a mineral or organic acid, such as HCl, HBr, HOAc, succinic acid, tartaric acid, ascorbic acid, and the like, which has a generally non-toxic counterion.

The term "oligopeptide" as used herein refers to a polypeptide having from two to about six amino acyl residues.

The term "effective amount" or "therapeutically effective amount" refers to the quantity of a compound of the invention necessary to treat a disorder mediated by overexcitation of the NMDA receptor/channel. "Treatment" as used herein includes prophylaxis (administration prior to damage) and therapy (administration during or after damage).

General Method:

One aspect of the invention is an NMDA channel blocker, selected from the group consisting of an oligo-peptide of the formula $X_a$-$X_1$-$X_2$-$X_3$-$X_4$-$X_5$-$X_6$, where $X_1$, and $X_6$ are each independently selected from the group consisting of natural and artificial amino acids, $X_2$, $X_3$, $X_4$, and $X_5$ are each independently selected from the group consisting of natural and artificial amino acids and a direct bond, wherein at least one of $X_1$, $X_2$, $X_3$, $X_4$, $X_5$, and $X_6$ is an aromatic amino acid if at least two of $X_2$, $X_3$, $X_4$, and $X_5$ are a natural or artificial amino acids; at least one of $X_1$, $X_2$, $X_3$, $X_4$, $X_5$, and $X_6$ is a guanidinium-containing amino acid, and $X_a$ is either H or acyl; and a compound of formula 1,

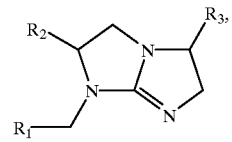

where $R_1$ is alkyl, alkenyl, or hydroxyalkyl, aminoalkyl, or alkoxy-alkyl; and $R_2$ and $R_3$ are each natural or artificial amino acid side chains; and pharmaceutically acceptable salts thereof; wherein said NMDA channel blocker exhibits selective NMDA channel blocking activity.

Another aspect of the invention is a method for treating exictotoxic neuronal death in a subject, comprising: providing an NMDA channel blocker compound selected from the group consisting of a oligopeptide of the formula $X_a$-$X_1$-$X_2$-$X_3$-$X_4$-$X_5$-$X_6$, where $X_1$ and $X_6$ are each independently selected from the group consisting of natural and artificial amino acids, $X_2$, $X_3$, $X_4$, and $X_5$ are each independently selected from the group consisting of natural and artificial amino acids and a direct bond, wherein at least one of $X_1$, $X_2$, $X_3$, $X_4$, $X_5$, and $X_6$ is an aromatic amino acid if at least two of $X_2$, $X_3$, $X_4$, and $X_5$ are a natural or artificial amino acids; at least one of $X_1$, $X_2$, $X_3$, $X_4$, $X_5$, and $X_6$ is a guanidinium-containing amino acid; and a compound of the formula

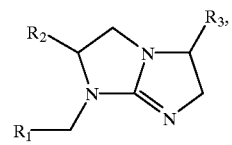

wherein $R_1$ is alkyl, alkenyl, or hydroxyalkyl, aminoalkyl, or alkoxy-alkyl; and $R_2$ and $R_3$ are each natural or artificial amino acid side chains; and pharmaceutically acceptable salts thereof; and administering an effective amount of said NMDA channel blocker compound to said subject.

Structurally, peptide NMDA blockers of the invention comprise peptides of two to about six amino acids in length which have between 1 and 6 arginines in combination with other natural or artificial amino acids. "Artificial" amino acids include optical isomers of natural amino acids, homologs such as phenylglycine and phenylleucine, halogenated and nitrated derivatives such as p-fluorophenylalanine and chloroalanine, naphthyl-alanine, and the like. Where at least one amino acid in the peptide is not arginine, the other amino acid(s) preferably include tryptophan. Of the latter peptides, any cysteine residue present will preferably be in the 3 position and any tryptophan residues present will preferably be in the 5 and/or 6 positions (where the N terminus of the peptide is position "1" and the C terminus of the peptide is position "6"). Most preferably, the peptides will not be acetylated.

In particular, peptides containing arginine in each one of six positions, cysteine at postion 3, or tryptophan at positions 5 and 6, display blockade activity well above the background level, operationally set at 25%. For example, peptides having the sequences RRRRRW, RRRRWW and RRCRWW, were selective for NMDA receptor channels, exhibited no blockade effect on non-NMDA glutamate receptors and remarkably, prevented neuronal cell death elicited by an excitotoxic insult in hippocampal cultures. It is noteworthy that the blockade potency of acetylated peptides was 3-fold lower than that of non-acetylated peptides, indicating a requirement of a free amino group for maximal blockade activity. Oligo-peptides shorter than six residues preferably have at least about 50% of their residues Arg, and preferably have at least one Trp residue, for example RR, RW, RRR, RRW, RRRW, RRCW, RRCRW, and the like.

To illustrate the activity of the inventive NMDA blockers, possible combinations of the most active residues at each position have been identified and assayed for NMDA blocking ability using a amphibian oocyte current blockade assay as described in Ferrer-Monteil and Montal, supra. Briefly, in the amphibian oocyte current blockade assay, human NMDA receptors are expressed in the oocytes. The receptors are stimulated in the cells by NMDA agonists. Agonist-induced current is the control against which current blockade levels achieved by incubating the oocytes with candidate NMDA blockers are measured.

NMDA receptor channel blocking peptides of the invention can be readily synthesized using such commonly used methods as t-Boc or Fmoc protection of alpha-amino groups. Both methods involve stepwise syntheses whereby a single amino acid is added at each step starting from the C terminus of the peptide (e.g., Coligan, et al., *Current Protocols in Immunology*, Wiley Interscience, 1991, Unit 9). Peptides of the invention can also be synthesized by various well known solid phase peptide synthesis methods, such as those described by Merrifield (*J Am Chem Soc* (1962) 85:2149), and Stewart and Young (*Solid Phase Peptides Synthesis*, Freeman, San Francisco, 1969, pp 27–62), using a copoly(styrene-divinylbenzene) polymer containing 0.1–1.0 mMol amines/g polymer.

On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on a "SEPHADEX G-15" or "SEPHAROSE" affinity column. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Alternatively, a particularly advantageous means for both identifying and producing peptides of the invention is the SCL approach described in Houghten, et al., *Nature* (1991) 354:84. Briefly, a synthetic combinatorial library of peptides is generated using either an iterative approach (coupling DCR (Houghten, et al., *Nature* (1991) 354:84, incorporated herein by reference) and simultaneous multiple peptide synthesis (SPMS) techniques) or a positional scanning approach (using standard Boc synthesis and SPMS techniques applied to mixtures of protected amino acids). Screened libraries yield peptides of interest by extraction on a resin substrate. The positional scanning approach is described in further detail infra.

To increase the efficacy of selected peptides so they can exert their physiological effect for longer periods of time, the following refinements to NMDA blockers of the invention can be made using techniques which those of ordinary skill in the art will be familiar with or can readily ascertain.

In order to increase the bioavailability of the peptides, the sequences corresponding to the most active NMDA blockers are synthesized using standard Fmoc or t-Boc chemistries but with amino acid derivatives in D-conformation. D-isomers of the NMDA blockers of the invention are desirable for their resistance to proteolytic degradation in vivo. It is well recognized that L-bond peptides are susceptible to proteolytic degradation, restricting their application as drugs. However, this obstacle has been successfully bypassed in some cases by synthesizing analogues which contain D-bond amino acids or non-natural amino acids. The addition of a single D-amino acid at the C-terminal position is enough to enhance the resistance to proteolytic degradation by exopeptidases, without significantly altering the secondary structure of the peptide. Resistance to endopeptidases can be achieved by including individual non-cleavable non-peptidic bonds in points in the peptide sequence that are specially sensitive to enzymatic degradation (Meyer et al., *J Med Chem* (1995) 38:3462–68; Guichard et al., *Peptide Res* (1994) 7:308–21). Reverse amide bonds Y(NHCO), reduced amide bonds Y(CH$_2$NH) or retro-reduced bonds Y(NHCH$_2$) can be used as surrogates of the amide link (CONH) in NMDA blockers of the invention. Reduced amide links are preferred, since they result only in minor-destabilization of a-helices (Dauber-Osguthorpe, et al., *Int J Pep Prot Res* (1991) 38:357–77).

Alternatively, NMDA blockers can be synthesized in all-D-conformations. All-D-peptides can be equally active as the original all-L-peptides (Merrifield, et al., *Ciba Foundation Symposium* 186:5–20 (1994); Wade, et al., *Proc Natl Acad Sci USA* (1990) 87:4761–65), capable of successfully resisting enzymatic degradation and less immunogenic than their all-L-analogues (King, et al., *J Immunol* (1994) 153:1124–31).

Alternatively, sequences with reduced peptide bonds in positions susceptible to proteolysis can be synthesized according to, for example, Meyer et al., *J Med Chem*, (1995) 38:3462–3468 (incorporated herein by reference). Briefly, such peptides are synthesized using a Fmoc/tert-butyl strategy, and the Y(CH$_2$NH) bonds, or reduced bonds, are introduced via reductive alkylation of the N-terminal amino group of the growing peptide with a Fmoc-Nα-protected amino aldehyde.

Additional NMDA blockers are formed by dimerizing two Cys-containing oligopeptide blockers by disulfide formation. For example, RCRCWW and RCRRWW can be dimerized by air oxidation in aqueous or aqueous/organic media, for example aqueous NH$_4$HCO$_3$ at weakly basic pH (e.g., about 8–8.5). Alternatively, peptides can be dimerized by dissolving in 0.1 M NH$_4$HCO$_3$ and treating with an excess of H$_2$O$_2$ (e.g., a 5 X excess) for about 15 minutes. Completeness of oxidation can be determined using the Ellman reagent. Alternative mild oxidation conditions are based on the oxidation by oxidized glutathione or by 5,5'-dithiobis(2-nitrobenzoic acid) in Tris buffer. Other oxidation conditions include the use of dimethyl sulfoxide, potassium ferricyanide, and/or iodine.

To confirm the distribution of NMDA blockers in vivo, each can be attached to a label which is detectable in vivo. For this purpose, the concentration of detectably labeled NMDA blockers which is administered should be sufficient such that the binding to the target protein is detectable compared to the background. Further, it is desirable that the detectably labeled NMDA blockers be rapidly cleared from the circulatory system in order to give the best target-to-background signal ratio.

For in vivo imaging, the type of detection instrument available is a major factor in selecting a given detectable label; e.g., a radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized.

Ideally, a radioisotope used for in vivo imaging will lack a particle emission, but produce a large number of photons in the 140–250 keV range, which can be readily detected by conventional gamma cameras. Typical examples of metallic ions which can be bound to the NMDA blockers of the invention are $^{111}$In, $^{97}$Ru, $^{67}$Ga, $^{68}$Ga, $^{72}$As, $^{89}$Zr, $^{90}$Y, and $^{201}$Tl.

NMDA blockers can also be labeled with a paramagnetic isotope for purposes of in vivo imaging, as in magnetic resonance imaging (MRI) or electron spin resonance (ESR) techniques. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

Bicyclic compounds of formula 1:

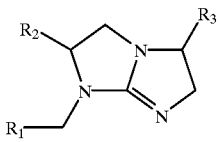

exhibit potent activity as NMDA channel blockers, where $R_1$ is alkyl, alkenyl, or hydroxyalkyl, aminoalkyl, or alkoxyalkyl, and $R_2$ and $R_3$ are each natural or artificial amino acid side chains, preferably wherein $R_2$ is derived from D-Arg, D-Ile, or L-t-butyl-Gly, and $R_3$ is derived from D-Arg or L-p-fluoro-Phe, and pharmaceutically acceptable salts thereof. Preferably at least one of $R_2$ and $R_3$ contains an aromatic ring, and at least one of $R_2$ and $R_3$ contains a guanidinium moiety. Presently preferred compounds include those wherein $R_1$ is —$(CH_2)_n CR_a R_b R_c$, where n is an integer from 0 to about 8, and $R_a$, $R_b$, and $R_c$ are each independently $CH_3$, $CH_3CH_2$, halo, or H, particularly where $R_2$ and $R_3$ are each independently selected from the group consisting of 3-guanadinylpropyl, 4-guanadinylbutyl, 3-guanadinylbutyl, 2-guanadinylethyl, 1-methylpropyl, 2-methylpropyl, propyl,

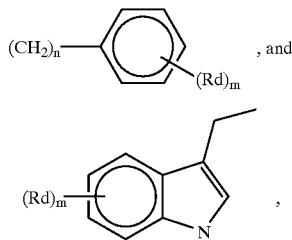

where m is an integer from 0 to 3, $R_d$ is a substituent selected from the group consisting of $CH_3$, $CF_3$, OH, $NH_2$, $NO_2$, SH, COOH, $CONH_2$, and halo. More preferred are those compounds wherein R2 and R3 are each independently 3-guanadinylpropyl, 1-methylpropyl, or 4-fluorobenzyl.

Compounds of formula 1 can be prepared by forming a dipeptide on a solid support, acylating the terminal amine, reducing the acylated dipeptide to provide a polyamine, and treating the polyamine with a reactive urea-forming agent such as thiocarbonyldiimidazole ("TCDI"). TCDI is believed to react with two of the nitrogen atoms to form a cyclic thiourea having a five-membered ring, which then reacts with the final nitrogen atom to provide a bicyclic guanidine derivative. For example, a first amino acid (having side chain $R_3$), e.g., L-4-fluorophenylalanine, is coupled to a MBHA resin support under standard conditions, and a second amino acid (having side chain $R_2$), e.g., D-Ile is coupled to the first. The resulting dipeptide is acylated with, for example, isobutyric acid, and reduced to provide an alkylated polyamine. The polyamine is treated with thiocarbonyldiimidazole, and cleaved from the resin with HF to provide the bicyclic guanidine derivative 2H-3-(4-fluorobenzyl)-7-(but-2-yl)-8-(3-methylbutyl)diazolidine-[1,2-b]dihydroimidazole:

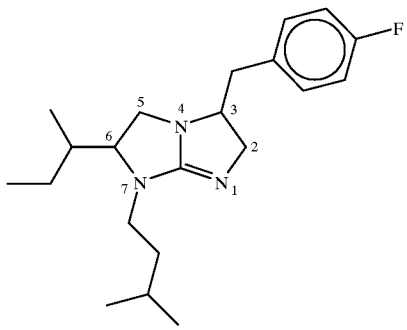

For ease of reference, compounds of formula 1 can be designated by noting the amino acids from which the $R_2$ and $R_3$ side chains derive, e.g., $R_1$=isobutyl, $R_2$=D-Arg, $R_3$=L-p-FPhe (where L-p-FPhe indicates L-p-fluoroPhe), although it is understood that an expression such as $R_2$=Arg (indicating an amino acid or amino acid derivative) refers only to the Arg side chain in the $R_2$ location.

Therapeutically useful compositions of NMDA blockers are prepared by mixing NMDA blockers of interest with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

Such compositions can be lyophilized for storage and will be reconstituted according to pharmaceutically acceptable means; i.e., suitably prepared and approved for use in the desired application. A sodium chloride free buffer is preferred for use as a reconstituting agent. Whatever its form, the composition product will be placed into sterile containers (e.g., ampules) for storage and transportation.

Clinically, the compounds of the invention will be useful in the same therapies which are or can be practiced with known NMDA antagonists, in particular memantine (1-amino-3,5-dimethyladmantane hydrochloride, CAS 41100-52-1). Protocols for administering the compounds of the invention (including dosing schedules and concentrations) will be similar to the clinical regimes for memantine administration (1 to 100 mg/day for humans, most typically 10–40 mg/day; see e.g., the following references incorporated herein by reference to illustrate known clinical regimes for the therapeutic use of memantine: Ambrozi and Danileczyk, *Pharmacopsychiatry* (1988) 21:144–46 (clinical trial in elderly patients with non-specific impaired cerebral function); Fischer, et al., *Arzneimittelforschung* (1977) 27:1487–89 (clinical trial in Parkinson's disease patients); Schneider, et al., *Dtsch Med Wochenschr* (1984) 109:987–990 (Parkinson's disease trial); Miltner, *Arzneimittelforschung* (1982) 32:1268–70 (clinical trial in patients with cerebral coma); Gortelmeyer and Erbler, *Arzneimittelforschung* (1992) 42:904–13 (clinical trial in dementia patients); and Chen, et al., *J Neurosci* (1992) 12:4427–36 (review)).

The potency and low immunogenicity of the inventive compounds will permit lower dosages and fewer applications to be provided as compared to memantine, depending on the patient's condition and the medical judgment of the clinician. In general, therefore, the concentration of a compound of the invention in a pharmaceutically acceptable carrier which produces a therapeutic benefit in a host that can also be provided by memantine, but is provided in lieu of memantine, is considered a "therapeutically effective dosage" of the inventive compound.

In addition to approved clinical trials of the inventive compounds in humans, their efficacy can be confirmed in various known animal models for cerebral impairments associated with NMDA receptor pathology, such as the rat ischemia model (e.g., Seif, et al., *Eur J Pharmacol* (1990) 185:19–24 and Block and Schwara, *Neurosci Lett* (1996) 208:41–44). Useful in vitro models for testing neuroprotective drug effects in cerebral neuronal cells are also known and include the chick embryo hypoxia model (e.g., Krieglstein, et al., *J Pharmacol Meth* (1988) 20:39–46) and the mammalian hippocampal neuronal system in which the inventive compounds were tested (e.g., Schinder, et al., supra). These references are each incorporated by reference to illustrate knowledge in the art concerning models of cerebral dysfunction. Those of ordinary skill in the art will be familiar with, or can readily ascertain, other suitable models for use in testing the compounds of the invention.

EXAMPLES

The following examples are provided as guidance for those of ordinary skill in the art, and are not intended to limit the scope of the claimed invention in any way. In the examples below, all experiments are performed at ambient conditions, and all reagents used per the manufacturer's recommendations, unless otherwise specified.

Example 1

(NMDA Receptor Channel Blocking Peptides)

(A) NMDA specific receptor channel blocking peptides ("NMDA blockers") were identified by screening synthetic combinatorial libraries (SCL) (see e.g., the library and peptide synthesis methods described in Ostresh, et al., *Meth Enzymol* (1996) 267:220–34, incorporated herein by reference) and assaying for blockade of agonist-evoked currents by the human NR1-NR2A NMDA receptor subunits expressed in amphibian (*Xenopus laevis*) oocytes (see, for example, the assay method described in Ferrer-Monteil and Montal, *METHODS:A Companion to Methods in Enzymology* (1994) 6:60–68, incorporated herein by reference). The NMDA blockers so identified block current at the NMDA receptor channel with a $K_i \sim 10$–50 nM, thereby rivaling the potency of clinically tolerated blockers such as memantine or dizolcipine (MK-801).

The results for the most active unacetylated peptides are summarized in FIG. 1. The amino acid sequences for these particular peptides of the invention are:

| RRRRRW | (#97) | RRCRRW | (#101) | RCRRWW | (#105) |
|--------|-------|--------|--------|--------|--------|
| RRRCRW | (#98) | RRCCRW | (#102) | RCRCWW | (#106) |
| RRRRWW | (#99) | RCRRRW | (#103) | RCCRRW | (#107) |
| RRRCWW | (#100) | RCRCRW | (#104) | RCCCRW | (#108) |
| RR | | RW | | RRR | |
| RRW | | RRRRRR | | | |

The most potent NMDA blockers were RRRRRW (#97), RRRRWW (#99) and RRRCRW (#98) (FIG. 1). Strikingly, a single tryptophan at the C-terminal position is sufficient to increase the blockade efficacy by 1000-fold, as evidenced by comparing the $K_i$ values for the RRRRRR (#111) and RRRRRW (#97) peptides.

Smaller peptides were also active, as shown in Table 1:

TABLE 1

| Sequence | $IC_{50}$ ($\mu M$) |
|----------|---------------------|
| RRWWRF | 3.7 ± 1.0 |
| RRWWIQ | 4.0 ± 1.0 |
| RRWWIN | 2.3 ± 0.3 |
| RRWWII | 2.0 ± 0.3 |
| RRWWIW | 1.0 ± 0.04 |
| RR | 12 ± 4 |
| RW | 10 ± 3 |
| RRR | 5 ± 6 |
| RRW | 2 ± 0.5 |
| RRRRRR | 0.5 ± 0.1 |
| rylfrr | 27 ± 4 |
| rrrwff | 40 ± 21 |
| rrrwrf | 6 ± 1 |
| rrrrww | 0.1 ± 0.4 |

In Table 1, D-amino acids are designated by lower case letter, for example "r" denotes D-Arg.

Figure 2:
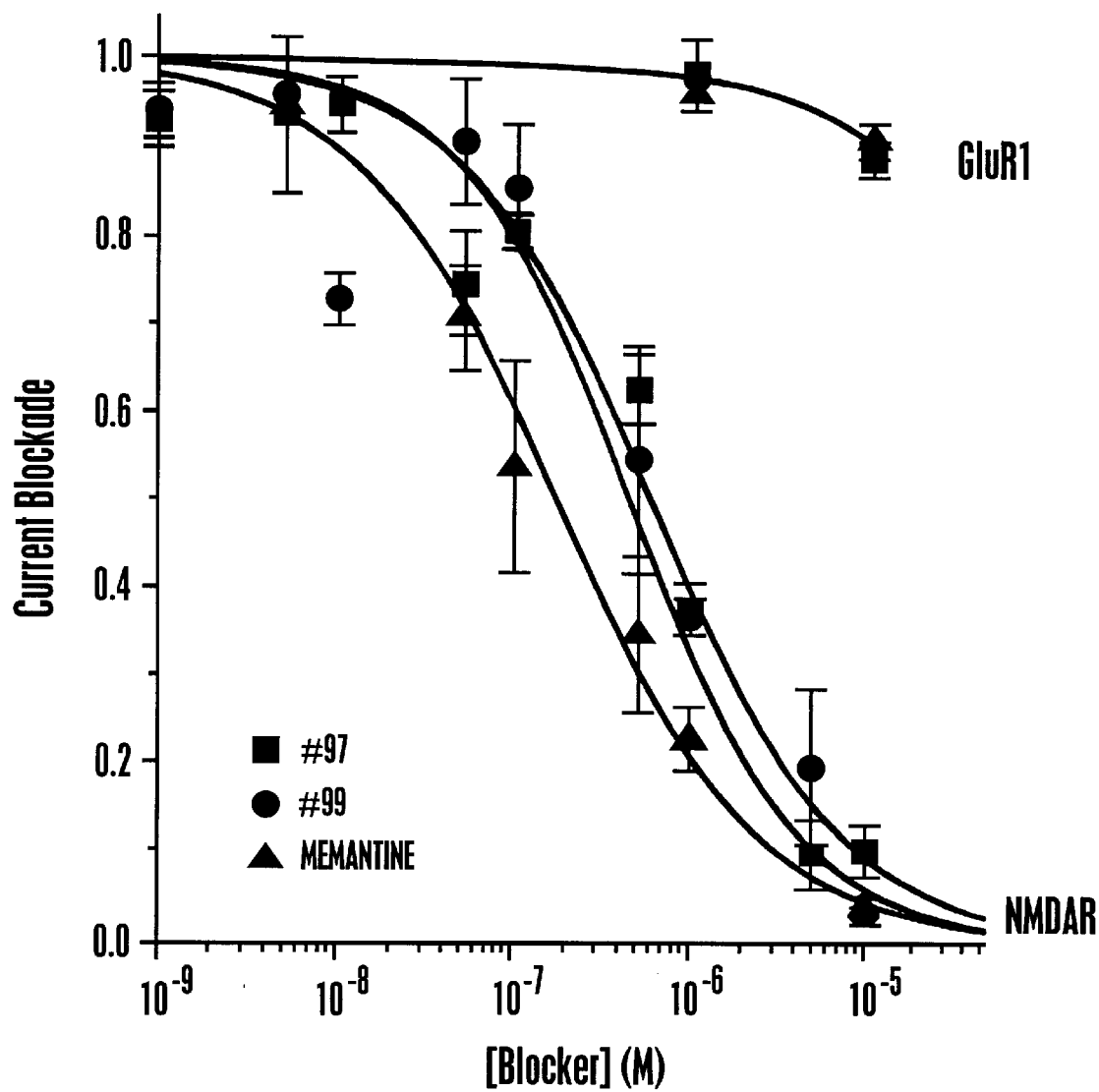
FIG. 2 is a graph comparing the current blockade achieved by various peptides of the invention (#97 ■ and #99 ●) as compared to memantine (▲), where all of the tested substances acted on NMDA receptors ("NMDAR") and glutamate receptors of the AMPA-receptor subunit GluR1 type ("GluR1") in amphibian oocytes.

(B) To examine the specificity of the blockade activity, the activity of the peptides on glutamate receptor channels of the non-NMDA subtype, specifically, the AMPA-receptor subunit GluR1, was tested. As shown in FIG. 1, NMDA receptor channels are highly sensitive to all the identified sequences; by contrast, AMPA receptor channels are weakly sensitive (excepting the response to the RRRCWW peptide, # 104). With respect to dose dependence, the current blockade exerted by a steady concentration of memantine is comparable to that of the same concentration of RRRRRW and RRRRWW (FIG. 2), indicating that dosing protocols for the peptides of the invention should be comparable to known dosing protocols for memantine.

Bona fide open channel blockers of the NMDA receptor transiently occlude the pore, acting with nanomolar inhibition constants and in a voltage-dependent fashion. To investigate whether the observed inhibitory activity of the identified peptides is due to blockade of open NMDA receptor channels, the voltage dependence of the blockade achieved by peptides of the invention was measured. NMDA blockers reduce glutamate-activated currents in oocyte cell cultures at negative membrane potentials. The extent of blockade decreases as the oocyte membrane is depolarized, indicating that the peptide senses the imposed electric field. Thus, the identified peptides satisfy the criteria set for open channel blockers.

Figure 3:
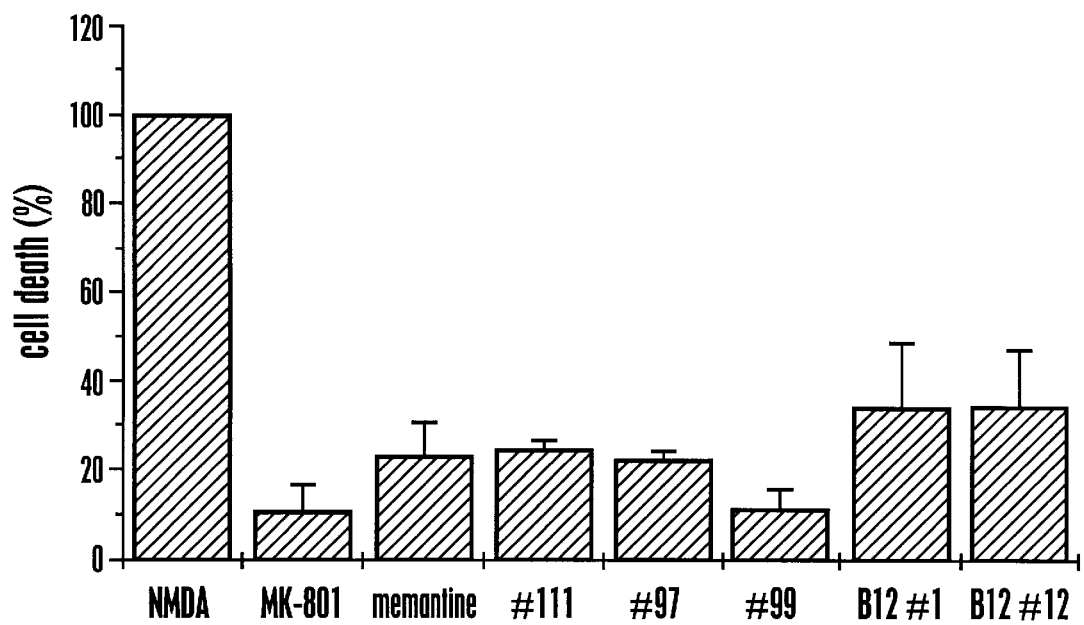
FIG. 3 is a bar graph comparing the reduction in NMDA-induced cell death among cultured hippocampal cells in the presence of MK-801 and memantine (known neuroprotectants) or peptides of the invention.
Figure 4:
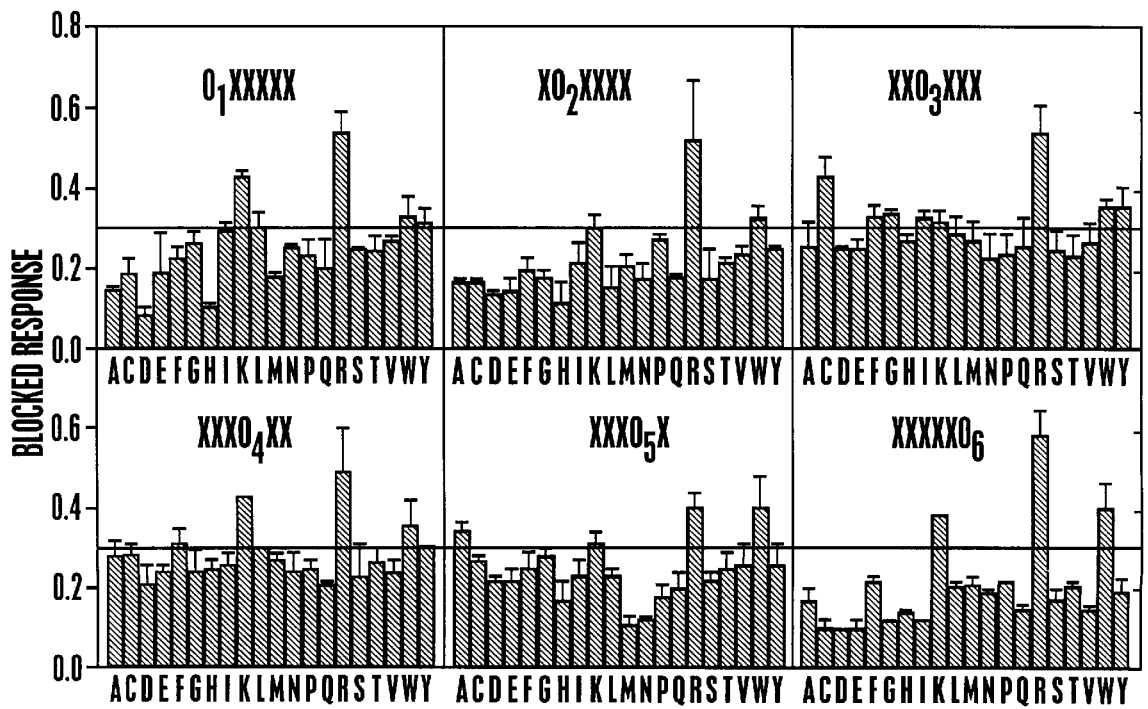
FIG. 4 is a chart depicting the results of a positional scan of a singly specified hexapeptide library.

Testing of the NMDA blockers of the invention in a hippocampal cell model for neurodysfunction (using the method described in Schinder, et al., *J Neurosci* (1996) 16:6125–33, incorporated herein by reference) yielded surprising results. Specifically, the NMDA blockers of the invention exert a substantial protective effect against cell death induced by exposure of cultured hippocampal neurons to glutamate agonists in the described model of neuronal cell death due to NMDA receptor dysfunction. In this model, neurons exposed to 200 μM NMDA for 20 minutes display extensive death that can be prevented by open channel blockers such as MK-801 or memantine (FIG. 3). This in vitro paradigm of excitotoxicity provides an assay of neuroprotection (see e.g., Schinder et al., supra and Deshpande, et al., *Arch Toxicol*, 69:384–390).

Strikingly, the identified peptides hexa-arginine (RRRRRR), RRRRRW, RRRRW and compounds B12#1 (acetylated MCRRKR) and B12#2 (acetylated LCRRKF) protected neurons from excitotoxic cell death (FIG. 3) in the neuronal cell death model. The $IC_{50}$ values (where 50% inhibition of cell death is achieved) for these peptides of the invention are in a range comparable to those for MK-801 or memantine. This constitutes further evidence that the inventive peptides are potent and selective neuroprotectants.

Example 2

(Synthesis of NMDA Receptor Channel Blocking Bicyclic Compounds)

(A) General Procedure: Compounds of formula 1 can be prepared using simultaneous multiple synthesis technology (R. A. Houghten, *Proc Natl Acad Sci USA* (1985) 82:5131–35). P-methylbenzhydrylamine (MBHA) resin (100 mg, 100–200 mesh) was sealed in a polypropylene mesh packet. Following neutralization with 5% diisopropyl-ethanolamine (DIEA) in dichloromethane (DCM), the resin was washed with DCM. The first Boc-protected amino acid (6 X, carrying side chain $R_3$) was coupled using hydroxy-benzotriazole (HOBt) (6 X) and diisopropycarbodiimide (DICI) (6 X, 0.1 M final conc. in dimethylformamide (DMF)). Following amino deprotection with 55% trifluoroacetic acid (TFA) in DCM, the packet was washed, neutralized, and a Boc-protected second amino acid (having side chain $R_2$) was coupled using the same conditions. After removing the Boc group, the dipeptide was acylated with a carboxylic acid (having side chain $R_1$) in the presence of DICI and HOBt.

The N-acylated dipeptide was then reduced in a 50 ml kimax tube under nitrogen. Boric acid (40 X) and trimethyl borate (40 X) were added, followed by 1M $BH_3$-THF (40 X). The tube was heated at 65° C. for 72 h, followed by quenching with MeOH. The resin was then washed with THF and MeOH. The amine-borane complex was dissociated by overnight treatment with piperidine at 65° C. Cyclization occurred following treatment of the reduced acylated dipeptide with thiocarbonyldiimidazole (0.5M in anhydrous DCM) for 15 min., followed by decanting the solution, adding anhydrous DCM, and shaking for 16 h. The cyclization procedure was repeated to ensure completion. Following cleavage from the resin with anhydrous HF (R. A. Houghten et al., *Int J Pept Protein Res* (1986) 27:673–78) in the presence of anisole, the desired compound was extracted and lyophilized.

(B) Using the procedure described in part (A) above, the following compounds were prepared:

2H-3-(4-fluorobenzyl)-7-(but-2-yl)-8-(3-methyl-butyl) diazolidine[1,2-b]dihydroimidazole;

2H-3-(3-guanidinopropyl)-7-(3-guanidinopropyl)-8-(3-methylbutyl)diazolidine[1,2-b]dihydroimidazole ($R_1$= isobutyl, $R_2$=D-Arg, $R_3$=D-Arg);

2H-3-(3-guanidinopropyl)-7-(but-2-yl)-8-(3-methyl-butyl)diazolidine[1,2-b]dihydroimidazole ($R_1$= isobutyl, $R_2$=D-Ile, $R_3$=D-Arg);

2H-3-(4-fluorobenzyl)-7-(3-guanidinopropyl)-8-(3-methylbutyl)diazolidine[1,2-b]dihydroimidazole ($R_1$= isobutyl, $R_2$=D-Arg, $R_3$=L-p-FPhe); and 2H-3-(4-fluorobenzyl)-7-(t-butyl)-8-(3-methyl-butyl) diazolidine[1,2-b]dihydroimidazole ($R_1$=isobutyl, $R_2$=t-butylGly, $R_3$=L-p-FPhe).

(C) Proceeding as set forth in part (A) above, a library of compounds was prepared using the following components:

First amino acid ($R_3$): L-Ala, L-Phe, L-Ile, L-Leu, L-Arg, L-Val, L-Tyr, D-Ala, D-Phe, D-Lys, D-Leu, D-Arg, D-Val, D-Tyr, L-α-aminobutyric acid, α-aminoisobutyric acid, D-norvaline, L-naphthylalanine, D-naphthylalanine, L-p-nitrophenylalanine, L-p-chloroPhe, D-p-chloroPhe, L-p-fluoroPhe, D-p-fluoroPhe, L-Lys (εAc), L- (3-pyridyl)-alanine, D-(3-pyridyl) alanine, L-cyclohexylglycine, L-α-t-butylGly, O-ethyl-L-Tyr, O-ethyl-D-Tyr, p-iodo-L-Phe, p-iodo-D-Phe, O-methyl-L-Tyr, and O-methyl-D-Tyr.

Second amino acid ($R_2$): L-Ala, Gly, L-Ile, L-Met, L-Arg, L-Val, D-Ala, D-Phe, D-Ile, D-Leu, D-Arg, D-Val, L-α-aminobutyric acid, L-norvaline, D-norvaline, L- (3-pyridyl) Ala, D-cyclohexylGly, and L-α-t-butylGly.

Acyl agent ($R_1$): ±2-methylbutyric acid, iso-valeric acid, 4-methylvaleric acid, cyclobutane carboxylic acid, cyclopentane carboxylic acid, 3-cyclo-pentylpropionic acid, 2-norboraneacetic acid, 2-ethyl-butyric acid, 2-methyl-4-nitro-1-imidazolepropionic acid.

(D) The compounds prepared in part (B) above were examined for activity against human brain NMDA receptors (composed of NR1 and NR2A subunits) expressed in oocytes. Ionic currents were activated by 200 μM L-glutamate (L-Glu) 20 μM glycine (Gly), at a holding potential $V_h$=80 mV. $Ba^{2+}$/flufenamic Ringer solution was supplemented with agonist and compounds of the invention, and blockade activity determined for each compound. Blocked response was calculated as 1- ($I_{cmpd}/I_{agonist}$), with currents measured at the end of the pulse, and the 50% inhibitory concentration ($IC_{50}$) determined. The results are shown in Table 2.

TABLE 2

Inhibitory Concentrations

| Compound | $IC_{50}$ (μM) |
| --- | --- |
| 2H-3-(4-fluorobenzyl)-7-(but-2-yl)-8-(3-methylbutyl)diazolidine[1,2-b]dihydroimidazole ($R_1$ = iBu, $R_2$ = D-Ile, $R_3$ = 1-pFPhe) | 1.2 ± 0.3 |
| 2H-3-(3-guanidinopropyl)-7-(3-guanidinopropyl)-8-(3-methylbutyl)diazolidine[1,2-b]dihydroimidazole ($R_1$ = iBu, $R_2$ = D-Arg, $R_3$ = D-Arg) | 4.2 ± 3.4 |
| 2H-3-(3-guanidinopropyl)-7-(but-2-yl)-8-(3-methylbutyl)diazolidine[1,2-b]dihydroimidazole ($R_1$ = iBu, $R_2$ = D-Ile, $R_3$ = D-Arg); | 11.8 ± 1.3 |
| 2H-3-(4-fluorobenzyl)-7-(3-guanidinopropyl)-8-(3-methylbutyl)diazolidine[1,2-b]dihydroimidazole ($R_1$ = iBu, $R_2$ = D-Arg, $R_3$ = L-pFPhe) | 6.1 ± 2.1 |
| 2H-3-(4-fluorobenzyl)-7-(t-butyl)-8-(3-methylbutyl)diazolidine[1,2-b]dihydroimidazole ($R_1$ = iBu, $R_2$ = t-BuGly, $R_3$ = L-pFPhe) | 2.2 ± 0.7 |

Example 3

(Screening Assay for NMDA Receptor Channel Blocking Compounds)

To find active sequences, positional scanning of synthetic combinatorial libraries (PS)-SCL can be used to address each separate single position of the sequence and increase the efficiency of the screening-selection process to identify compounds which possess the blockade activity of the invention (see e.g., the method described in C. Pinilla et al., *Biotechniques* (1992) 13:901–05). In particular, the (PS)-SCL greatly simplifies screening of massive peptide libraries such as those described herein (for example, a singly specified non-acetylated hexapeptide library defined by NH$_2$-O$_1$XXXXX-NH$_2$, where 0 is a defined position with one of the 20 naturally-occurring amino acids (aa)s and X represents an approximately equimolar mixture of the 20aas, is made up of 49,521,980 peptides). A separate mixture is prepared for each O$_1$XXXXX, XO$_2$XXXX, XXO$_3$XXX, . . ., XXXXXO$_6$, and each mixture of compounds is assayed. For each position (O$_1$, O$_2$, etc.), one or more residues having the most apparent activity are selected. For example, if the O1XXXXX pool having Ser in the first position demonstrates activity, Ser is selected for the first position. If Arg and Trp demonstrate activity in the second position, both could be selected. One or more residues are selected for each position, and most or all of the resulting possibile oligopeptides are then synthesized and assayed.

Compounds with positive activity are identified as follows: saturating concentrations of L-glutamate and glycine are applied to hippocampal cell cultures to minimize distraction by peptides competing for the agonist and/or co-agonist binding sites; a negative voltage is applied across the cell membranes to target the selection towards compounds that sense the imposed electric field, i.e. open channel blockers having the characteristics and functions of the peptides of the invention described herein.

Figure 5:
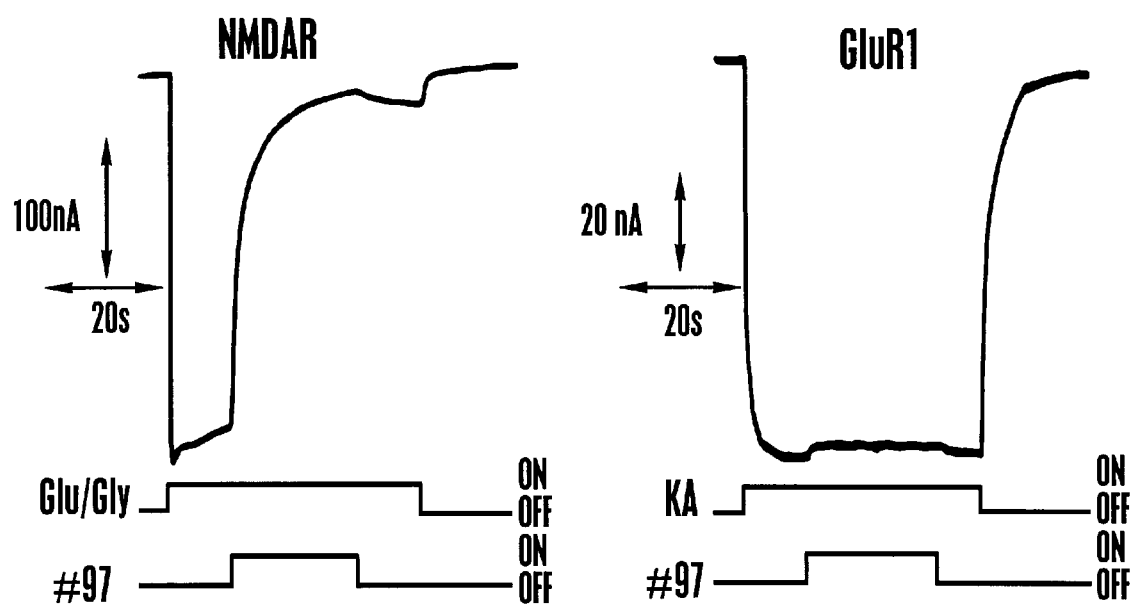
FIG. 5 is a schematic depicting the response of NMDA receptors (left) and GluR1 receptors (right) in amphibian oocytes to pulses of glutamate/glycine or peptide #97 of the invention.

An example of how the assay method is performed follows, with reference to FIG. 5. Inward currents were elicited upon perfusion of oocytes expressing NMDA receptors with 200 μM L-glutamate/20 μM glycine according to the pulse protocol displayed under the current trace (top line) in FIG. 5. Evoked currents (agonist-pulse ON) increased rapidly to a steady level that was sharply attenuated upon perfusion with peptide # 97 (bottom line, library-pulse ON). The glutamate-elicited signal is recovered when the library was perfused with an agonist/Ringer solution (middle line, library-pulse OFF). The L-glutamate evoked response was terminated when the agonist was washed out (middle line, pulse OFF).

Channel blocking activity on the part of candidate NMDA blockers selected according to the (PS)-SCL method described can be confirmed in any suitable model for testing neuroprotection of cerebral neuronal cells, such as the hippocampal cell death assay described supra.

The invention having been fully described, potential modifications and extensions of the invention will be apparent to those of ordinary skill in the art. All such modifications and extensions are believed to be within the scope of the invention.

What is claimed:

1. An NMDA channel blocker, selected from the group consisting of
a oligopeptide of the formula:

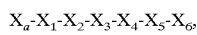

wherein X$_1$, and X$_6$ are each independently selected from the group consisting of natural and artificial amino acids,
X$_2$, X$_3$, X$_4$, and X$_5$ are each independently selected from the group consisting of natural and artificial amino acids and a direct bond, wherein
at least one of X$_1$, X$_2$, X$_3$, X$_4$, X$_5$, and X$_6$ is an aromatic amino acid if at least two of X$_2$, X$_3$, X$_4$, and X$_5$ are a natural or artificial amino acids;
at least one of X$_1$, X$_2$, X$_3$, X$_4$, X$_5$, and X$_6$ is a guanidinium-containing amino acid; and
X$_a$ is either H or acyl; and
a compound of formula 1,

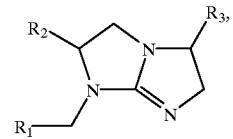

wherein R$_1$ is alkyl, alkenyl, or hydroxy-alkyl, aminoalkyl, or alkoxy-alkyl; and
R$_2$ and R$_3$ are each natural or artificial amino acid side chains; and pharmaceutically acceptable salts thereof;
wherein said NMDA channel blocker exhibits selective NMDA channel blocking activity.

2. The oligopeptide of claim 1, wherein Xa is acetyl.

3. The oligopeptide of claim 2, wherein said oligopeotide is selected from the group consisting of Ac-MCRRKR and Ac-LCRRKF.

4. The oligopeptide of claim 1, wherein Xa is H.

5. The oligopeptide of claim 4, wherein X$_6$ comprises an indole-containing amino acid.

6. The oligopeptide of claim 4, wherein X$_6$ comprises D-Trp or L-Trp.

7. The oligopeptide of claim 6, wherein at least one of said guanidinium-containing amino acids comprises D-Arg or L-Arg.

8. The oligopeptide of claim 7, wherein said oligopeptide is selected from the group consisting of; RRRRW, RRRCRW, RRRRWW, RRRCWW, RRCRRW, RRCCRW, RCRRRW, RCRCRW, RCRRWW, RCRCWW, RCCRRW, and RCCCRW.

9. The oligopeptide of claim 1, wherein said oligopeptide is selected from the group consisting of RR, RW, RRR, RRW, RRRRRR, D-Arg-D-Arg-D-Arg-D-Trp-D-Arg-D-Phe, and D-Arg-D-Arg-D-Arg-D-Arg-D-Trp-D-Trp.

10. The compound of claim 1, wherein R$_1$ is —(CH$_2$)$_n$CR$_a$R$_b$R$_c$, where n is an integer from 0 to about 8, and R$_a$, R$_b$, and R$_c$ are each independently CH$_3$, CH$_3$CH$_2$, halo, or H.

11. The compound of claim 1, wherein R$_2$ and R$_3$ are each independently selected from the group consisting of 3-guanadinylpropyl, 4-guanadinylbutyl, 3-guanadinylbutyl, 2-guanadinylethyl, 1-methylpropyl, 2-methylpropyl, propyl,

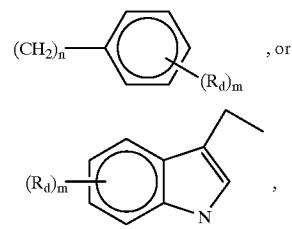

where m is an integer from 0 to 3, R$_d$ is a substituent selected from the group consisting of CH$_3$, CF$_3$, OH, NH$_2$, NO$_2$, SH, COOH, CONH$_2$, and halo.

12. The compound of claim 11, wherein R2 and R3 are each independently 3-guanadinylpropyl, 1-methylpropyl, or 4-fluorobenzyl.

13. The compound of claim 1, wherein said compound is selected from the group consisting of 2H-3-(4-fluorobenzyl)-7-(but-2-yl)-8-(3-methylbutyl)diazolidine[1,2-b]dihydroimidazole:

2H-3-(3-guanidinopropyl)-7-(3-guanidinopropyl)-8-(3-methylbutyl)diazolidine[1,2-b]dihydroimidazole;

2H-3-(3-guanidinopropyl)-7-(but-2-yl)-8-(3-methylbutyl)diazolidine[1,2-b]dihydroimidazole;

2H-3-(4-fluorobenzyl)-7-(3-guanidinopropyl)-8-(3-methylbutyl)diazolidine[1,2-b]dihydroimidazole; and 2H-3-(4-fluorobenzyl)-7-(t-butyl)-8-(3-methylbutyl)diazolidine[1,2-b]dihydroimidazole;

and a pharmaceutically acceptable salt thereof.

14. A method for treating exictotoxic neuronal death in a subject, comprising:

providing an NMDA channel blocker compound selected from the group consisting of a oligopeptide of the formula:

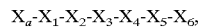

wherein $X_1$, and $X_6$ are each independently selected from the group consisting of natural and artificial amino acids, $X_2$, $X_3$, $X_4$, and $X_5$ are each independently selected from the group consisting of natural and artificial amino acids and a direct bond, wherein at least one of $X_1$, $X_2$, $X_3$, $X_4$, $X_5$, and $X_6$ is an aromatic amino acid if at least two of $X_2$, $X_3$, $X_4$, and $X_5$ are a natural or artificial amino acids; at least one of $X_1$, $X_2$, $X_3$, $X_4$, $X_5$, and $X_6$ is a guanidinium-containing amino acid; and a compound of the formula:

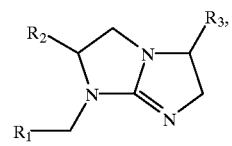

wherein $R_1$ is alkyl, alkenyl, or hydroxyalkyl, aminoalkyl, or alkoxy-alkyl; and $R_2$ and $R_3$ are each natural or artificial amino acid side chains;

an pharmaceutically acceptable salts thereof; and administering an effective amount of said NMDA channel blocker compound to said subject.

15. The method of claim 14, wherein said NMDA channel blocker compound is selected from the group consisting of AC-MCRRKR, Ac-LCRRKF, RRRRW, RRRCRW, RRRRWW, RRRCWW, RRCRRW, RRCCRW, RCRRRW, RR, RW, RRR, RRW, RCRCRW, RCRRWW, RCRCWW, RCCRRW, RCCCRW, 2H-3-(4-fluorobenzyl)-7-(but-2-yl)-8-(3-methylbutyl)diazolidine[1,2-b]dihydroimidazole: 2H-3-(3-guanidinopropyl)-7-(3-guanidinopropyl)-8-(3-methylbutyl)diazolidine[1,2-b]dihydroimidazole; 2H-3-(3-guanidinopropyl)-7-(but-2-yl)-8-(3-methyl-butyl)diazolidine[1,2-b]dihydroimidazole; 2H-3-(4-fluorobenzyl)-7-(3-guanidinopropyl)-8-(3-methylbutyl)diazolidine[1,2-b]dihydroimidazole; and 2H-3-(4-fluorobenzyl)-7-(t-butyl)-8-(3-methylbutyl)diazolidine[1,2-b]dihydroimidazole; and a pharmaceutically acceptable salt thereof.

* * * * *

UNITED STATES PATENT AND TRADEMARK OFFICE
CERTIFICATE OF CORRECTION

PATENT NO. : 6,251,854 B1
DATED : June 26, 2001
INVENTOR(S) : Montal et al.

Page 1 of 1

It is certified that error appears in the above-identified patent and that said Letters Patent is hereby corrected as shown below:

Column 14,
Line 21, please replace "oligopeotide" with -- oligopeptide --;

Column 16,
Line 14, please replace "an" with -- and --; and
Line 19, please replace "AC-MCRRKR" with -- Ac-MCRRKR --.

Signed and Sealed this

Fifteenth Day of January, 2002

Attest:

JAMES E. ROGAN
Attesting Officer
Director of the United States Patent and Trademark Office